United States Patent
Thomke et al.

(10) Patent No.: US 9,549,762 B2
(45) Date of Patent: Jan. 24, 2017

(54) PREVENTION OF RE-USE OF A MEDICAL DEVICE

(71) Applicant: Stryker Trauma SA, Selzach (CH)

(72) Inventors: Roland Thomke, Bellach (CH); Hans-Peter Bigler, Gasel (CH); Philippe Lehmann, Lamboing (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 822 days.

(21) Appl. No.: 13/755,441

(22) Filed: Jan. 31, 2013

(65) Prior Publication Data

US 2013/0158551 A1 Jun. 20, 2013

Related U.S. Application Data

(62) Division of application No. 11/974,172, filed on Oct. 11, 2007, now Pat. No. 8,382,804.

(30) Foreign Application Priority Data

Oct. 13, 2006 (EP) .................................... 06122309

(51) Int. Cl.
*A61B 5/04* (2006.01)
*A61B 17/64* (2006.01)

(52) U.S. Cl.
CPC ............ *A61B 17/6466* (2013.01); *A61B 90/92* (2016.02); *A61B 2090/0814* (2016.02); *Y10T 403/4933* (2015.01)

(58) Field of Classification Search
CPC ......... A61B 17/60; A61B 17/62; A61B 17/64; A61B 17/6416; A61B 17/6425; A61B 17/6433; A61B 17/6441; A61B 61/645; A61B 17/6458; A61B 17/6466; A61B 17/6475; A61B 17/6483; A61B 17/6491; A61F 2250/009
See application file for complete search history.

(56) References Cited

U.S. PATENT DOCUMENTS 3,346,464 A * 10/1967 Ernst ........................ C12Q 1/22
250/282
3,360,338 A * 12/1967 Edenbaum ................ A61L 2/28
106/31.64

(Continued)

FOREIGN PATENT DOCUMENTS

DE      20314173 U     12/2003
DE   102004043325 A1 *  4/2005   ......... A61B 17/6466

(Continued)

OTHER PUBLICATIONS

Translation of FR2493138A1.*
Translation of DE102004043325A1.*
European Search Report, EP 06 122 309.5 dated Mar. 14, 2007.

*Primary Examiner* — Lynnsy Summitt
(74) *Attorney, Agent, or Firm* — Lerner, David, Littenberg, Krumholz & Mentlik, LLP

(57) ABSTRACT

A disposable medical device is especially an articulation for the relative positioning of fixation bars or of pins of an external fixator, having at least a clamping means to be introduced into the medical device, the clamping means comprises an element that alters its appearance when being heated over a threshold temperature, thus giving optical or mechanical information that the device should not be used a second time.

22 Claims, 8 Drawing Sheets

(56) References Cited

U.S. PATENT DOCUMENTS

| | | | | |
|---|---|---|---|---|
| 3,862,824 | A * | 1/1975 | Chapman | G01N 31/226 422/420 |
| 4,414,166 | A * | 11/1983 | Charlson | B23K 26/324 264/249 |
| 4,483,334 | A * | 11/1984 | Murray | A61B 17/60 403/391 |
| 4,514,361 | A * | 4/1985 | Hirsch | G01N 31/226 422/119 |
| 4,604,996 | A * | 8/1986 | Nunamaker | A61D 9/00 54/82 |
| 4,620,533 | A * | 11/1986 | Mears | A61B 17/645 606/54 |
| 4,759,713 | A | 7/1988 | Heiss | |
| 4,893,618 | A * | 1/1990 | Herzberg | A61B 17/60 606/54 |
| 5,269,784 | A | 12/1993 | Mast | |
| 5,330,483 | A | 7/1994 | Heaven et al. | |
| 5,393,161 | A * | 2/1995 | Mata | A61B 17/6416 403/112 |
| 5,472,415 | A * | 12/1995 | King | A61L 2/26 604/110 |
| 5,507,826 | A * | 4/1996 | Besselink | A61B 17/7001 606/78 |
| 5,578,041 | A * | 11/1996 | Nash | A61D 9/00 606/54 |
| 5,593,425 | A * | 1/1997 | Bonutti | A61B 17/0401 606/220 |
| 5,752,954 | A * | 5/1998 | Mata | A61B 17/645 606/53 |
| 5,813,992 | A | 9/1998 | Henwood | |
| 5,891,144 | A * | 4/1999 | Mata | A61B 17/6466 606/54 |
| 5,916,816 | A * | 6/1999 | Read | A61L 2/28 422/119 |
| 5,990,199 | A * | 11/1999 | Bealing | A61L 2/28 106/31.13 |
| 6,206,844 | B1 | 3/2001 | Reichel | |
| 6,342,054 | B1 * | 1/2002 | Mata | A61B 17/62 606/54 |
| 6,565,564 | B2 * | 5/2003 | Hoffman | A61B 17/6466 606/59 |
| 6,613,049 | B2 * | 9/2003 | Winquist | A61B 17/6458 606/54 |
| 6,616,664 | B2 * | 9/2003 | Walulik | A61B 17/645 600/230 |
| 6,716,212 | B1 * | 4/2004 | Pickens | A61B 17/645 606/54 |
| 6,736,775 | B2 * | 5/2004 | Phillips | A61B 17/02 600/234 |
| 6,913,666 | B1 * | 7/2005 | Aeschlimann | B29C 66/7392 156/303.1 |
| 7,241,074 | B2 * | 7/2007 | Thomke | A61B 17/645 24/545 |
| 7,261,713 | B2 * | 8/2007 | Langmaid | A61B 17/6458 606/59 |
| 7,335,205 | B2 * | 2/2008 | Aeschlimann | A61B 17/00491 433/173 |
| 7,422,593 | B2 * | 9/2008 | Cresina | A61B 17/66 606/54 |
| 7,491,008 | B2 * | 2/2009 | Thomke | A61B 17/645 403/316 |
| 7,527,626 | B2 * | 5/2009 | Lutz | A61B 17/60 606/54 |
| 7,585,299 | B2 * | 9/2009 | Rezach | A61B 17/7041 606/246 |
| 7,699,879 | B2 * | 4/2010 | Sherman | A61B 17/68 606/289 |
| 7,967,820 | B2 * | 6/2011 | Bonutti | A61B 17/0401 606/64 |
| 8,172,840 | B2 * | 5/2012 | Murner | A61B 17/6466 403/289 |
| 8,182,483 | B2 * | 5/2012 | Bagnasco | A61B 17/6483 606/58 |
| 8,187,274 | B2 * | 5/2012 | Schulze | A61B 17/6441 606/56 |
| 8,206,388 | B2 * | 6/2012 | Thomke | A61B 17/6466 606/324 |
| 8,235,994 | B2 * | 8/2012 | Hollawell | A61B 17/6416 606/59 |
| 8,241,285 | B2 * | 8/2012 | Mullaney | A61B 17/6466 606/324 |
| 8,298,266 | B2 * | 10/2012 | Miller | A61B 17/705 606/250 |
| 8,444,643 | B2 * | 5/2013 | Thomke | A61B 17/645 606/253 |
| 8,496,657 | B2 * | 7/2013 | Bonutti | A61B 17/0401 606/62 |
| 8,523,858 | B2 * | 9/2013 | Lessig | A61B 17/645 24/135 R |
| 8,523,923 | B2 * | 9/2013 | Thomke | A61B 17/60 24/335 |
| 8,540,713 | B2 * | 9/2013 | Zandona | A61B 17/6466 606/324 |
| 8,685,023 | B2 * | 4/2014 | Dorawa | A61B 17/6466 606/59 |
| 8,728,078 | B2 * | 5/2014 | Miller | A61B 17/6466 606/324 |
| 8,734,446 | B2 * | 5/2014 | Miller | A61B 17/6466 606/277 |
| 8,764,750 | B2 * | 7/2014 | Zgonis | A61B 17/62 606/57 |
| 8,808,289 | B2 * | 8/2014 | Busch | A61B 17/6466 403/72 |
| 8,821,491 | B2 * | 9/2014 | Chreene | A61B 17/6466 606/54 |
| 8,827,997 | B2 * | 9/2014 | Cremer | A61B 17/6466 606/324 |
| 8,827,998 | B2 * | 9/2014 | Dorawa | A61B 17/6466 606/54 |
| 8,840,611 | B2 * | 9/2014 | Mullaney | A61B 17/6466 269/254 CS |
| 8,932,330 | B2 * | 1/2015 | Bonutti | A61B 17/0487 606/232 |
| 8,945,129 | B2 * | 2/2015 | Dominik | A61B 17/60 606/54 |
| 9,050,135 | B2 * | 6/2015 | Dominik | A61B 17/6466 |
| 9,089,368 | B2 * | 7/2015 | Oesch | A61B 17/645 |
| 9,138,260 | B2 * | 9/2015 | Miller | A61B 17/60 |
| 9,186,179 | B2 * | 11/2015 | Mullaney | A61B 17/6466 |
| 2002/0032443 | A1 | 3/2002 | Sherman et al. | |
| 2006/0039750 | A1 * | 2/2006 | Thomke | A61B 17/645 403/385 |
| 2006/0155276 | A1 * | 7/2006 | Walulik | A61B 17/6416 606/59 |
| 2006/0177263 | A1 * | 8/2006 | Thomke | A61B 17/645 403/322.4 |
| 2006/0229605 | A1 * | 10/2006 | Olsen | A61B 17/6416 606/54 |
| 2006/0255521 | A1 * | 11/2006 | Brunner | A61B 17/6466 269/86 |
| 2007/0012372 | A1 * | 1/2007 | Jay | A61B 17/685 138/95 |
| 2007/0038217 | A1 * | 2/2007 | Brown | A61B 17/6466 606/57 |
| 2007/0270833 | A1 * | 11/2007 | Bonutti | A61B 17/0401 606/28 |
| 2007/0293860 | A1 * | 12/2007 | Oesch | A61B 17/645 606/60 |
| 2010/0023057 | A1 * | 1/2010 | Aeschlimann | A61B 17/0401 606/246 |
| 2010/0130959 | A1 * | 5/2010 | Boyd | A61B 17/60 604/513 |
| 2011/0112533 | A1 * | 5/2011 | Venturini | A61B 17/6466 606/54 |
| 2012/0296335 | A1 * | 11/2012 | Mullaney | A61B 17/6466 606/59 |

(56) References Cited

U.S. PATENT DOCUMENTS

| | | | |
|---|---|---|---|
| 2013/0144289 A1* | 6/2013 | Dorawa | A61B 17/6466 606/54 |
| 2014/0276818 A1* | 9/2014 | Wong | A61B 17/645 606/56 |
| 2015/0119886 A1* | 4/2015 | Milella, Jr. | A61B 17/6466 606/59 |
| 2015/0238228 A1* | 8/2015 | Langenfeld | A61B 17/66 606/105 |

FOREIGN PATENT DOCUMENTS

| | | | |
|---|---|---|---|
| EP | 0303436 | 2/1989 | |
| FR | 2767669 | 8/1997 | |
| FR | 2864889 | 1/2004 | |
| GB | FR 2493138 A1 * | 5/1982 | A61B 17/60 |
| WO | 9524166 | 9/1995 | |
| WO | 9837819 | 9/1998 | |
| WO | 0064366 | 11/2000 | |
| WO | 2004112625 | 12/2004 | |
| ZA | WO 9832385 A1 * | 7/1998 | A61B 17/6466 |

\* cited by examiner

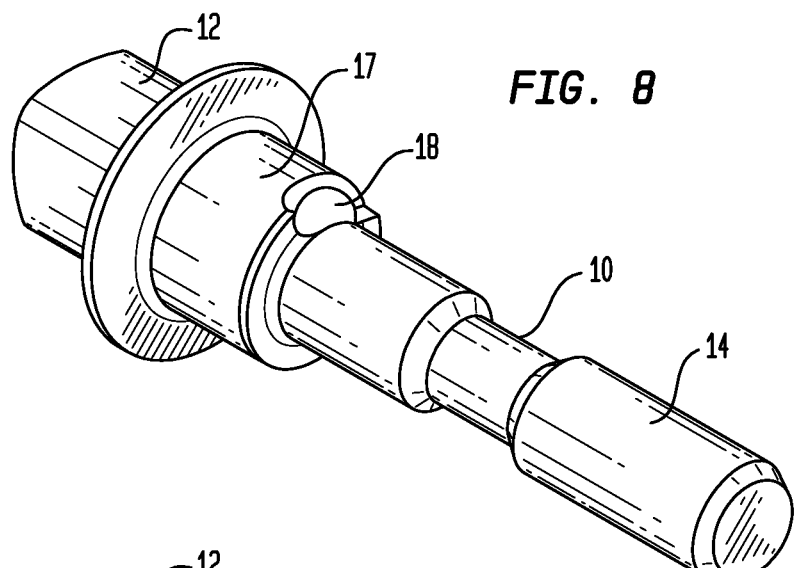
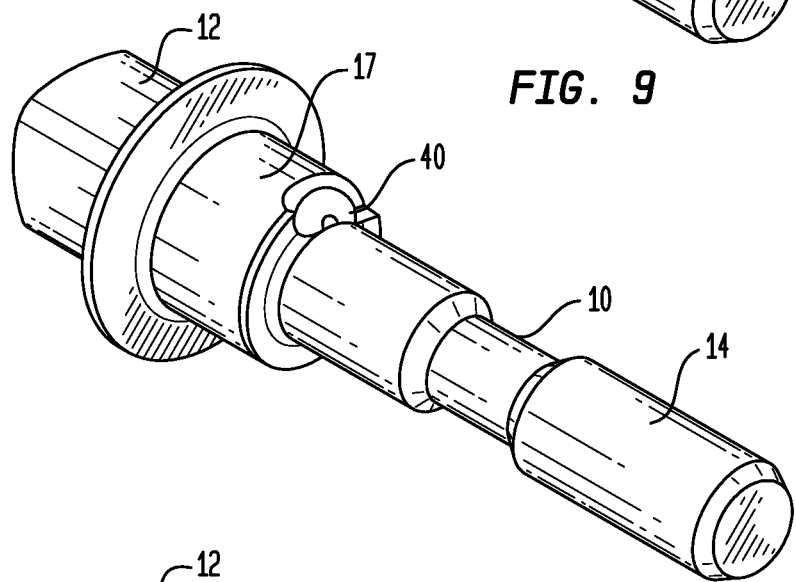
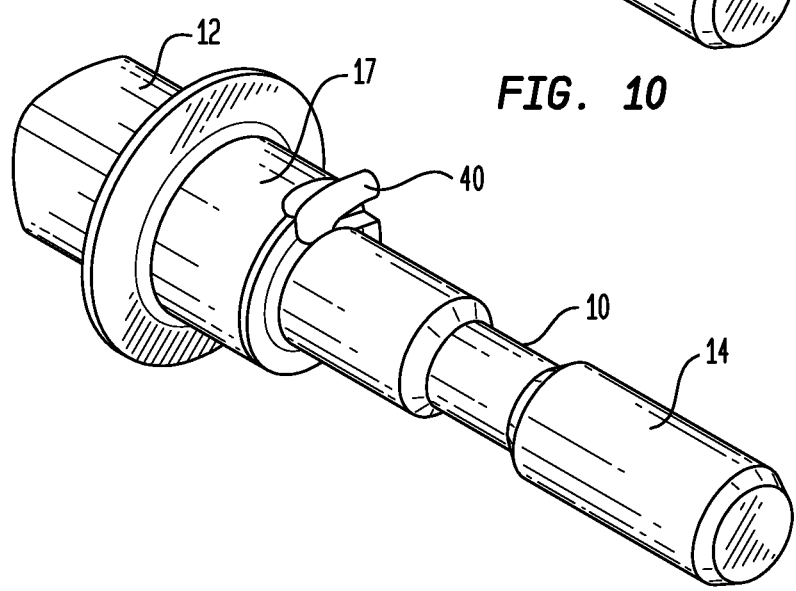

PREVENTION OF RE-USE OF A MEDICAL DEVICE

CROSS-REFERENCE TO RELATED APPLICATIONS

The present application is a divisional of U.S. patent application Ser. No. 11/974,172, filed on Oct. 11, 2007, which claims priority from European Patent Application No. 06122309.5 filed Oct. 13, 2006, all of which are incorporated herein by reference.

BACKGROUND OF THE INVENTION

The present invention relates to a disposable medical device with a sterilization indicator to prevent its re-use.

Disposable medical devices are designed for single use and should not be used twice or more times. They are very common in the field of medical devices. Usually written or symbolic warnings are applied to the packing of such a device or on the device itself. Such warnings display to the medical personnel that the device is for single-use only. However there is the potential that such warnings may be overlooked. Even though such medical devices may be sterilised, there is a risk of transmitting infectious diseases.

U.S. Pat. No. 6,206,844 relates to a single-use ultrasonic surgical device. This device comprises a hub that becomes irregular upon sterilization in a steam sterilizer or in an autoclave. As a result this device cannot be attached to a handpiece assembly again. U.S. Pat. No. 5,472,415 relates to a trial implant which deforms upon re-sterilization.

BRIEF SUMMARY OF THE INVENTION

An aspect of the present invention is to provide a disposable medical device with a design which prevents the medical device from being used a second time.

According to the invention there is provided a device having at least a clamping means to be introduced into the medical device, said clamping means comprises an element that alters when being heated over a threshold temperature, thus giving optical or mechanical information that the device should not be used a second time.

BRIEF DESCRIPTION OF THE DRAWINGS

The drawings will be explained in greater detail by means of a description of an exemplary embodiment, with reference to the following figures:

FIG. 8 shows a central shaft of the third embodiment in a perspective view without an insert/bracket;

FIG. 9 shows the central shaft of FIG. 8 with a bracket in a first starting position according to the third embodiment of the present invention;

FIG. 10 shows the central shaft of FIG. 8 with a bracket in a second position according to the third embodiment of the present invention;

DETAILED DESCRIPTION

Figure 3:
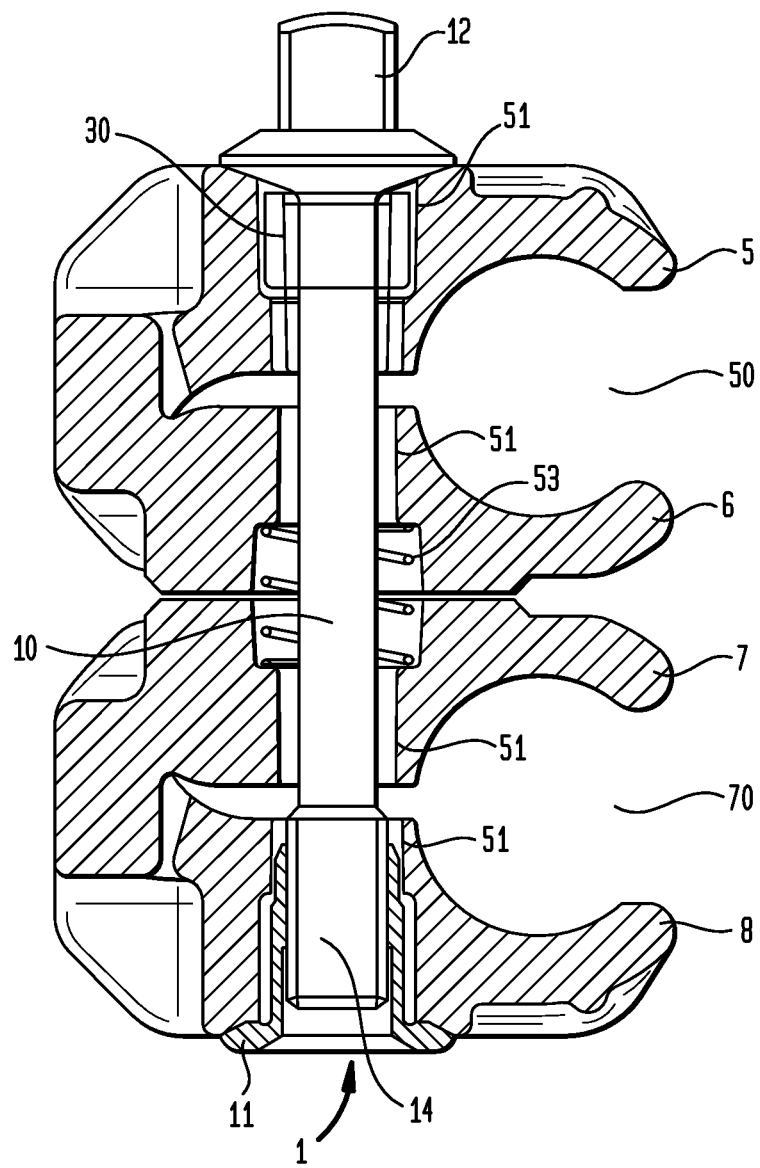
FIG. 3 shows a cross section of an articulation with a device according to a second embodiment of the present invention.

FIG. 3 shows a disposable articulation device for relative positioning of fixation bars or of pins of an external fixator. Such an articulation may be an articulation according to U.S. Pat. No. 6,080,153. The articulation comprises at least a plurality of pairs of jaws 5, 6 and 7, 8 and clamping means 1. The jaws 5, 6, 7, 8 have openings 51 that receive a central shaft 10 of the clamping means 1. The central shaft 10 comprises on a first end a head 12 and is connected to a threaded stop 11 on a second end.

The jaws 5, 6, 7, 8 are being positioned relative to each other in a manner that openings 50, 70 result. Said openings 50, 70 are intended to receive bars or pins of an external fixator or any other medical device. If said bars and pins have been brought into the desired position, the central shaft 10 and the threaded stop 11 will be tightened by means of a wrench or screwdriver. The jaws 5, 6, 7, 8 of a disposable device are preferably made of plastic material and the central shaft 10 is preferably made out of a metallic material, especially aluminium, titanium or stainless steel. However, it is clear that the invention is related to any medical device, preferably to articulation for external fixators.

Figure 1:
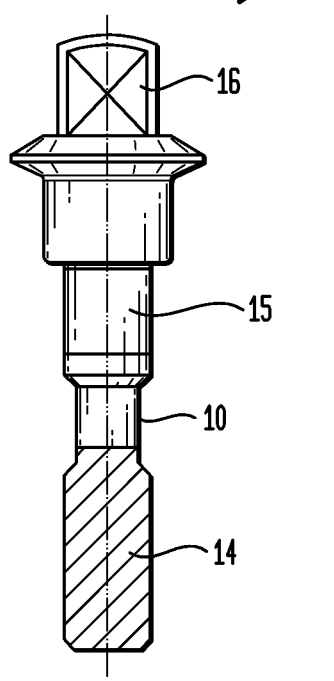
FIG. 1 shows a partial cross section of a central shaft according to a first embodiment of the present invention.

FIG. 1 shows a first embodiment of such a central shaft 10 as usable in an articulation device according to FIG. 3 in detail. Essentially the central shaft of FIG. 1 comprises a threaded section 14, a cylindrical section 15 and a head portion 16. The only mandatory element of this element 10 is the head section 16, i.e. a section which is visible from outside or is at least in contact with the outer surroundings.

Figure 2:
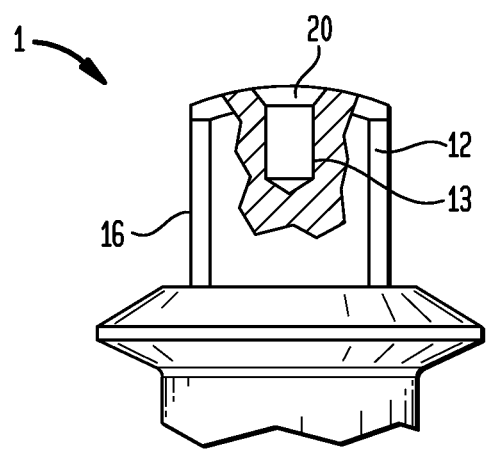
FIG. 2 shows a partial cross section of a detail of the embodiment of FIG. 1.

FIG. 2 shows the head portion 16 according to the first embodiment of the present invention. The head portion 16 comprises the head 12, which is provided with an opening 13 that extends along the central axis of the central shaft. The opening 13 is preferably a center bore with a diameter that is clearly recognisable by medical personnel. Preferably the diameter is between 1 mm and 5 mm. However larger diameters are also possible because they increase the visibility.

An insert 20 is introduced into the opening 13. The insert 20 is preferably made out of a material having a melting point being higher than room temperature, preferably higher than 60 degree Celsius but lower than the usual sterilization temperature, i.e. lower than 120 degree Celsius, and typically lower than 140 degree Celsius. Such a material can be a resin or wax like material. The insert 20 is preferably a pre-produced insert that will be pressed into the opening 13 or a cast insert that will be cast or injected directly into the opening 13. If the insert 20 is introduced into the opening 13, the person e.g. medical personnel using such a device will therefore recognise a circular point on the surface of the head 16.

It is essential that the material used for the insert will have a rigid state at room temperature. As soon as a certain temperature will be applied to the insert, its state will change from the rigid state to a viscous state. If the temperature increases further the insert becomes liquid. Preferably the insert becomes liquid at a temperature of 90° C. However the insert shall not change its state if a warm temperature e.g. 40° C. or even 60° C. is applied. Therefore the central shaft is still washable without a change of the state of the insert. This is needed in the production chain or if the medical personnel does wound care on a patient in order to ensure hygienic standards.

In case the central shaft 10 or other parts of this disposable articulation will be cleaned and sterilized by means of an autoclave, which uses temperatures over 130° C., or any other cleaning means in order to be used a second time, the insert will change its state, due to its material properties. Thereby the whole or at least some parts of the insert will flow out of the opening 12. An empty or partly filled opening is therefore the result of a sterilization process and indicates that this device should not be used again. The difference from the filled opening 12 to the empty opening 12 is clearly visible and this enables the medical personnel to distinguish between a new disposable articulation that may be used and a sterilized disposable articulation that may not be used again. This simple identification of wrongly sterilized disposable articulation enhances the quality of a hospital and eases the working process of the medical personnel.

In a further embodiment according to the present invention the inner surface of the opening 12 is colored with a color that is different form the color of the central shaft 10 and the insert 20. As an example the insert 20 may have a green color. This indicates that the articulation is new and has not been used. If the central shaft 10 is sterilized the insert 20 will flow out, and the surface of the opening 13 is visible. The surface is colored for example in red and indicates that the central shaft 10 has been sterilized. The use of such different colors enhances the recognizability of sterilization process of the disposable articulation.

In a still further embodiment according to the present invention (not shown) the insert is made out of a material that changes its color when being exposed to higher temperatures. Such an insert may be an insert as disclosed above. But the insert may also be replaced by a painted section. Thereby the parts or even the whole head 12 are covered with paint. The paint changes its color when it is exposed to specific temperature that is applied by an autoclave or other cleaning means. Such a change in color also allows that a medical personnel recognises a sterilizing process of a disposable articulation. In this embodiment it is possible that the material does not flow out of the head 12.

It is clear to the person skilled in the art that such an opening 12 and such an insert 20 may be applied to any other disposable medical device.

FIG. 3 shows the disposable articulation in combination with a rectangular insert 30 according to a second embodiment of the present invention.

In this embodiment one of the jaws, here jaw 5, comprises an opening intended to receive the rectangular insert 30.

Figure 5:
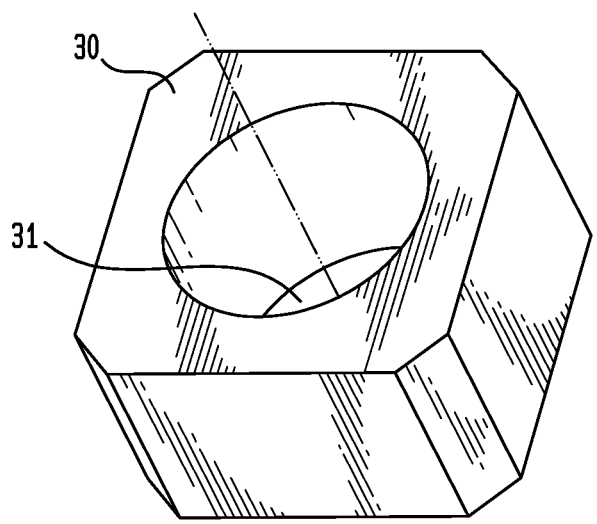
FIG. 5 shows a part of the device of FIG. 3.

An example of the rectangular insert 30 is shown in a perspective view in FIG. 5. Thereby the rectangular insert 30 has preferably a cuboid shape and comprises an opening 31 for receiving the central shaft 10.

The rectangular insert 30 is placed in the opening 51. Thereby the central axes of the opening 51 and of the opening 31 are preferably coaxial. The central shaft 10 is then introduced into the opening 51 and 31. The insert 30 is within a cavity inside jaw 5 and does not rotate, when the screw function of the shaft is activated, i.e. the clamp is clamping a rod.

The rectangular insert is preferably made out of the same material as the insert of the first embodiment.

In case the disposable articulation will be heated i.e. sterilized by an autoclave or any other suitable cleaning means, the rectangular insert 30 will change its state from rigid to liquid. Thereby the liquid insert 30 will flow from its previous position into the interior of the jaws, preferably into functional parts such as the spring 53. As soon as the temperature reaches room temperature the distributed material of the insert will become rigid again at that position where it flowed to. This will lead to a form closure, at least between the central shaft 10 and the jaw, where to opening 51 is allocated, here jaw 5. Due to that form closure it is not possible to operate the central shaft because it is blocked against rotation and subsequent translation. Therefore multiple use of the disposable articulation will be avoided.

FIG. 5 shows the rectangular insert 30 of the second embodiment in combination with a different articulation device. In this embodiment a multiplicity of clamping means 1 are distributed over the circumference of the articulation device. The function and the alignment of the clamping elements and the central shaft 10 respectively and the inserts 30 are as described by means of FIG. 4.

It is clear to the person skilled in the art that said insert may have various different shapes. Good results were also achieved with an insert that has a tubular shape and is arranged in the same manner as described. The tubular insert will be distributed in a higher degree as the rectangular insert. This provides an improved form closure.

Figure 4:
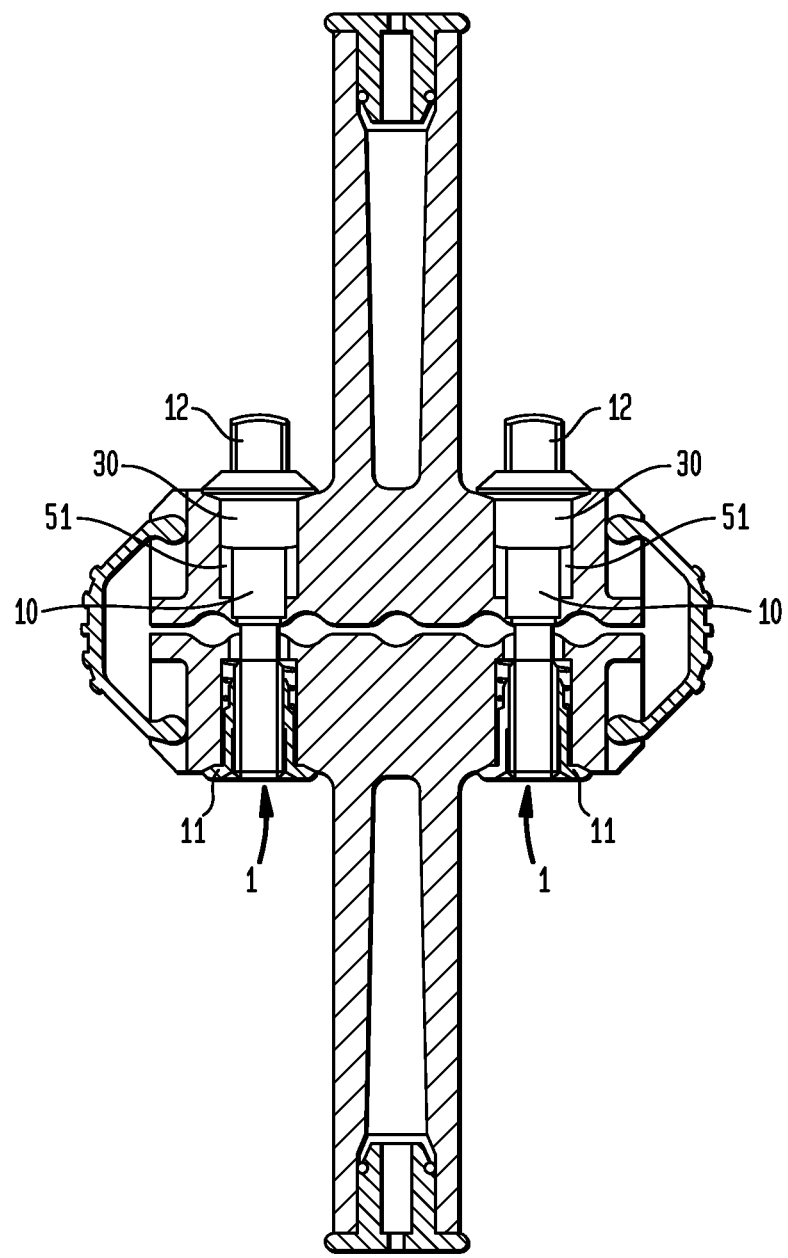
FIG. 4 shows a cross of another articulation with the device of FIG. 3.
Figure 6:
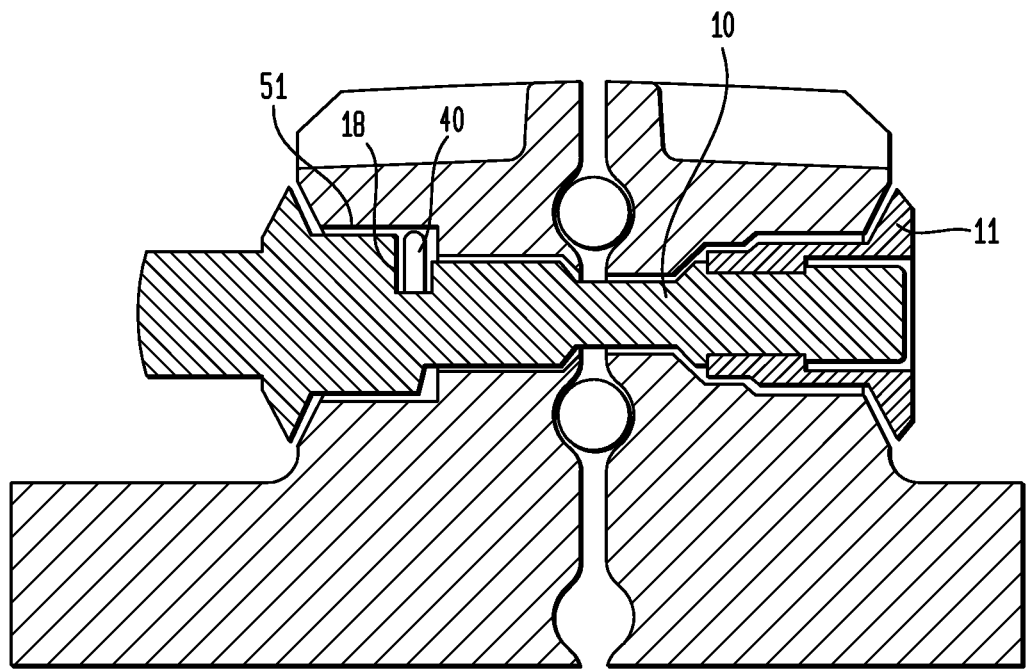
FIG. 6 shows a partial cross section of a device according to a third embodiment of the present invention.
Figure 7:
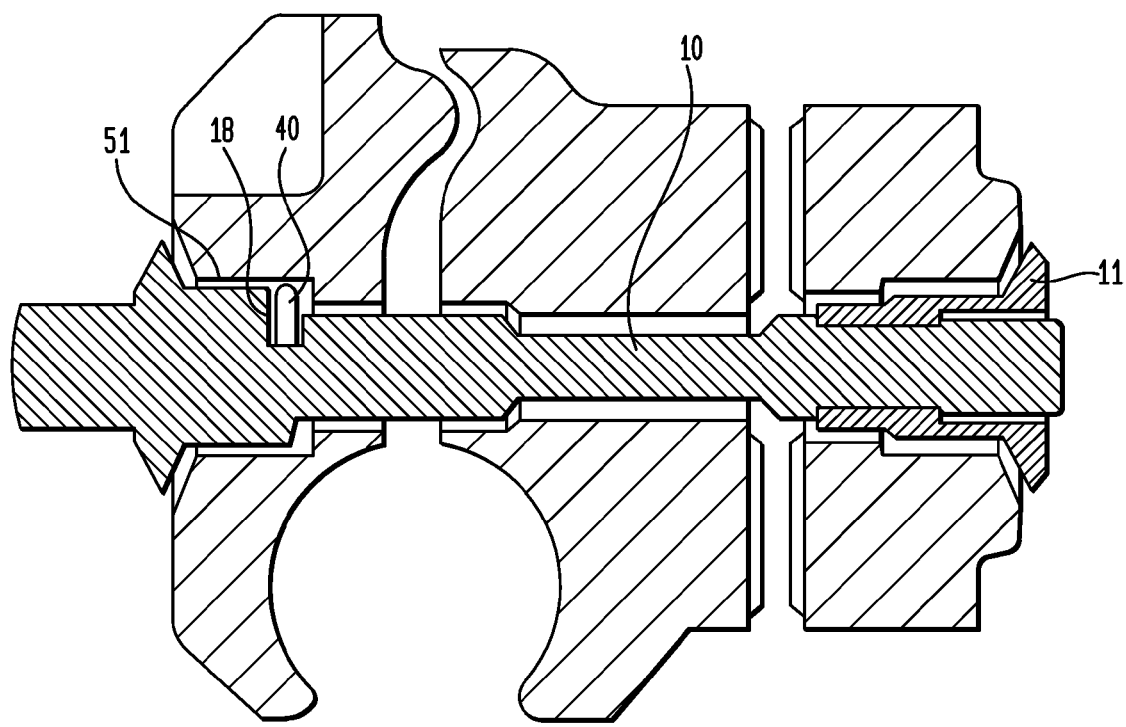
FIG. 7 shows a further cross section of a device with the third embodiment of the present invention.

FIG. 6 shows a partial cross section of a device according to a third embodiment of the present invention, wherein the clamping element is similar to the device according to FIG. 4. FIG. 7 shows a partial cross section of a device according to the third embodiment of the present invention, wherein the clamping element is similar to the device according to FIG. 3.

Before referring to these drawings in detail, it is referred to FIG. 9, showing a central shaft in combination with an element according to a third embodiment of the present invention. The element here is a shape memory alloy or polymer bracket 40 or a wire being able to take in two different positions or geometries. A first starting position describes the geometric shape at room temperature (FIG. 9). A second position (FIG. 10) describes the geometric shape after the temperature has crossed a (higher) threshold temperature once.

Figure 11:
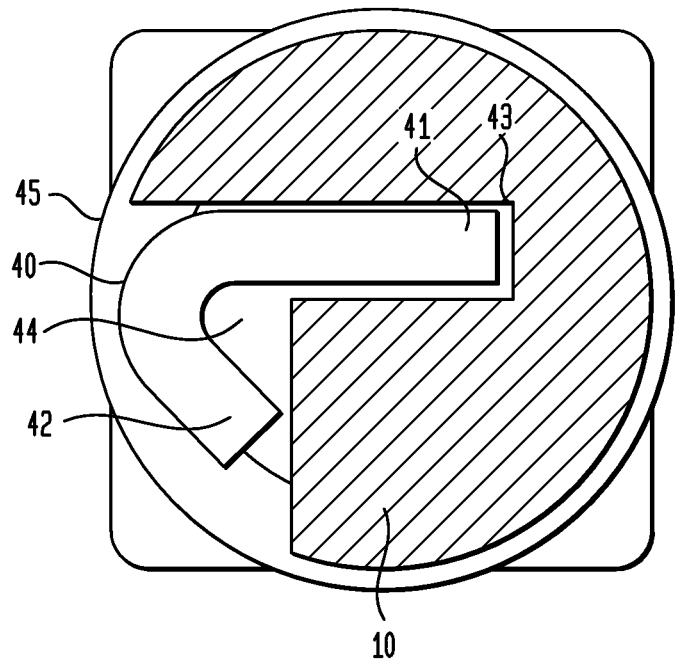
FIG. 11 shows a cross section of the central shaft and the corresponding parts with the bracket in the first starting position according to the third embodiment of the present invention.
Figure 12:
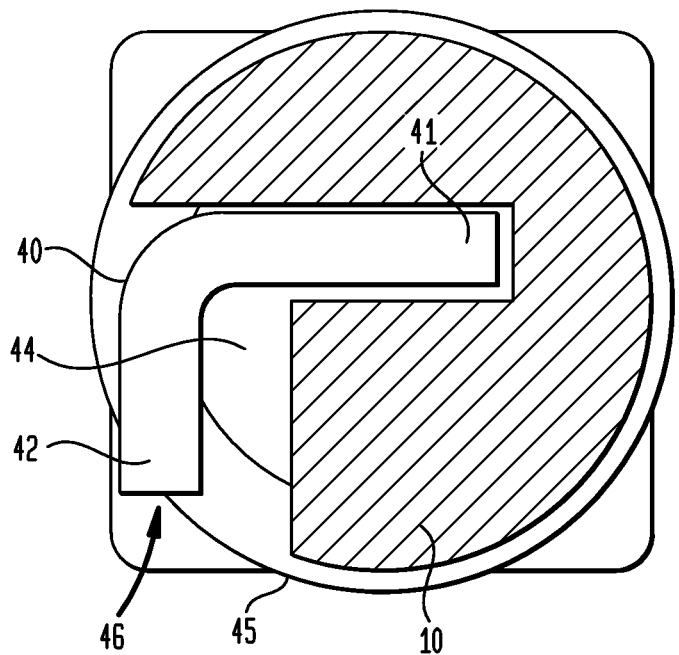
FIG. 12 shows a cross section of the central shaft and the corresponding parts with the bracket in the second position.
Figure 13:
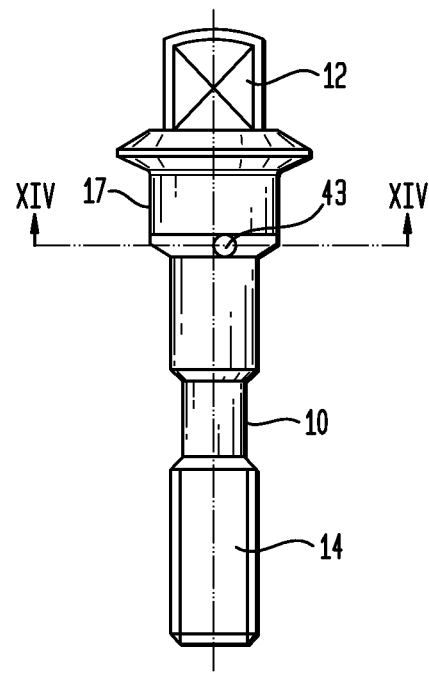
FIG. 13 shows a side view of the central shaft of FIG. 8 without a bracket.

FIG. 11 shows a bracket 40 according to the first initial position. The bracket 40 comprises a first leg 41 and a second leg 42. The second leg 42 is arranged angular to the first leg 41 and especially forms an acute angle. The first leg 41 of the wire like bracket is introduced into a corresponding recess 43 within the central shaft 10. The position of the recess 43 is slightly offset to a radial line through the center of the shaft 10. The second leg is bent towards the middle of the shaft 10 and is located within an opening 44. Opening 44 cuts a section of the shaft 10 and allows the second leg 42 to be accommodated inside the circumference 45 of the shaft 10. Due to its material properties, the bracket 40 is able to be deformed from the first starting position to a second position when the bracket 40 is exposed to a temperature that is higher than the certain threshold temperature. Preferably said threshold temperature is around 80° C. In the first starting position the angle between the first leg 41 and the second leg 42 is preferably between 45° and 75° as can be seen in FIG. 11. FIG. 12 shows the bracket 40 according to the second position. The second leg 42 is now arranged in a right angle to the first leg 41. Now the free end 46 of the leg 42 is clearly outside said circumference 45 of the shaft 10.

FIGS. 6 and 7 show the clamping member 1 introduced into the openings 51 of the jaws. In a first section 52 the opening 51 in the jaw has a rectangular cross-section. The bracket 40 is arranged on the central shaft 10, which comprises an opening 18 designed to receive parts of said bracket 40. In the mounted condition the bracket 40 lies in that section of the opening 51 of the jaw that has the rectangular cross-section.

FIG. 8 shows a central shaft 10 of the third embodiment in a perspective view without an insert/bracket, thus clearly showing the recess 18 allowing accommodation of the insert. FIG. 9 shows the central shaft 10 of FIG. 8 with a bracket 40 in a first starting position according to the third embodiment of the present invention. FIG. 10 shows the central shaft of FIG. 8 with the bracket 40 in a second blocking position after use and sterilization.

In the first starting position, the bracket 40 is arranged in the opening 18 (see FIG. 8) of the central shaft in a manner that it does not project over a cylindrical surface 17 of the central shaft 10. This allows a rotational movement of the central shaft 10 in the opening 51 in order to tighten the clamping means 1.

As soon as the temperature crosses the threshold temperature, the bracket 40 will change from the first starting position into the second position. In the second position the angle between the first leg 41 and the second leg 42 is preferably 90°. As it may be seen in FIG. 11 the second leg 42 projects over the cylindrical surface 17 of the central shaft. Additionally the second leg also touches the sidewalls of the opening 51. Due to this the rotational movement is blocked by the second leg 42 in either rotational direction. Therefore the clamping means cannot be tightened any more and the disposable articulation may not be used a second time.

The bracket 40 is made out of a memory metal with a one-way effect. This means that the bracket is not formed back to the first starting position when the temperature crosses the threshold temperature. Preferably the materiel is chosen out of the group of alloys encompassing but not limiting copper-zinc-aluminium, copper-aluminium-nickel or nickel-titanium.

It is also possible that the bracket 40 is made out of memory polymers.

Figure 14:
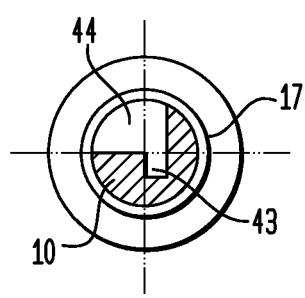
FIG. 14 shows a detail in a cross section along line XIV-XIV of FIG. 13.

FIG. 14 and FIG. 15 show in a side view and a detailed cross section, respectively, the possible form of the recess 43 to accommodate one leg 41 of the insert and the opening 44 to accommodate the second leg 42 of the insert 40.

In a further embodiment not shown in the drawings the bracket also comprises a first and a second leg. In the first starting position the two legs are arranged in an angle of 90°. Both ends of the legs of bracket are arranged in a groove that is tangentially arranged in the central shaft 10. Therefore both legs are outside the circumference 45/17 of the shaft 10. As soon as the threshold temperature will be crossed, the shape of the bracket 40 will change to the second position. In the second position the two legs and their axes become coaxial. Thereby the bracket lies in the groove of the central shaft. Any rotational movement of the central shaft will be blocked.

In a further embodiment according to the present invention, the rectangular opening 51 comprises a groove that is on the sidewalls of the opening. The groove is essentially perpendicular to the central axis of the central shaft. If the bracket 40 changes its shape into the second position on end of second leg 42 penetrates said groove. As already described above any rotational movement of the central shaft is blocked, but additionally the central shaft is also blocked by the bracket against movements in direction of the central axis, since the leg also engages said groove.

In the described examples of embodiments similar to the third embodiment, in the first position, the bracket 40 or other insert either engages the shaft 10 and freely rotates with it. In the second position the bracket changes its form and engages the clamping means upon leaving the circumference 17 of the shaft 10, i.e. the accommodation area of free rotation. In the other design the bracket 40 is accommodated in the clamping means itself and does not interfere within the circumference of rotation of the shaft. Upon crossing the threshold temperature the bracket changes its form and then engages said rotational circumference zone. This can be especially achieved, if the cross section of the shaft at the position of the bracket is not symmetrical in relation to its longitudinal axis. This allows the bracket to firmly engage the shaft 10 in a position, where the not symmetrical recess allows the bracket 40 to freely take its second position.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A disposable medical device, for an articulation element for a relative positioning of fixation bars, rods or pins of an external fixator, comprising:
   at least one clamp having first and second jaws for positioning the rods or pins to be introduced into the medical device and having an opening between the first and second jaws;
   a rigid insert arranged in the opening of the clamp in a manner allowing clamping of the bars, rods or pins;
   wherein the insert is made of a material having characteristics that are altered when being heated over a threshold temperature, wherein the threshold temperature is higher than 50° C. and less than 140° C.; and
   wherein the insert material alters its state from a rigid state to a viscous state at the threshold temperature so that the insert material is arranged in the opening in a manner preventing the clamping of the bars, rods or pins.

2. The device according to claim 1, wherein the insert is made out of a material chosen from a group of materials having a melting point at the threshold temperature.

3. The device according to claim 1, wherein the threshold temperature is higher than 60° C.

4. The device according to claim 1, wherein the threshold temperature is higher than 80° C.

5. The device according to claim 1, wherein the insert alters its state from the rigid state to a liquid state when being exposed to a temperature higher than said threshold temperature.

6. The device according to claim 5, wherein at least parts of the insert material flow along a central shaft extending through the first and second jaws and establishes a locking closure between the central shaft and a functional element of the device as soon as the insert reaches a rigid state again.

7. The device as set forth in claim 1 wherein the insert changes color when more viscous upon being exposed to the threshold temperature.

8. The device as claimed in claim 1 wherein the insert material is a resin or wax material.

9. The device as claimed in claim 1 wherein the insert material has a melting point less than 120° C.

10. A disposable medical device, especially an articulation for a relative positioning of fixation bars or of pins of an external fixator, comprising
    at least one clamp to be introduced into the medical device and having a central shaft and an opening with a clearance;
    an insert arranged in the opening of the clamp;
    wherein the insert encompasses the central shaft of the clamp at least partially;
    wherein the insert alters its state from a rigid state to a viscous or liquid state when being exposed above a threshold temperature, wherein the threshold temperature is higher than 50° C. and less than 140° C.;
    wherein at least parts of the insert can flow along the central shaft and establish a locking closure between the central shaft and a functional element of the device as soon as the temperature falls below the threshold temperature and the insert reaches a rigid state again; and
    wherein the functional element is a spring.

11. The device according to claim 10, wherein the insert is made out of a material chosen form a group of materials having a melting point at the threshold temperature.

12. The device according to claim 10, wherein the threshold temperature is higher than 60° C.

13. The device according to claim 10, wherein the threshold temperature is higher than 80° C.

14. The device as claimed in claim 10 wherein the insert material is a resin or wax material.

15. The device as claimed in claim 10 wherein the insert material has a melting point less than 120° C.

16. A disposable medical device, for an articulation element for a relative positioning of bars or pins of an external fixator, comprising:
    at least one clamp comprising first and second jaws each having an opening therethrough, a locking shaft extending through the opening in the first and second jaws, the locking shaft having a first cross-section smaller than a second cross-section of the opening in the first and second jaw, the first jaw having an enlarged area surrounding the opening;
    an insert mounted in the enlarged area of the first jaw, the insert having an opening therein for receiving the locking shaft; and
    the insert made of a material that is solid at room temperature but is flowable at a temperature above 50° C., the insert capable of filing at least part of a volume between the first and second cross-sections upon being heated to the temperature above 50° C. and less than 140° C.

17. The device as set forth in claim 16 wherein flow of the flowable material into at least part of the volume between the first and second cross-section establishes a locking closure between the locking shaft and the first or second jaw upon solidification of the flowable material.

18. The device as set forth in claim 16 further comprising a spring acting on at least one of the first and second jaws, the insert flowable material contacts the spring and forms a locking closure between the spring and the locking shaft.

19. The device according to claim 16, wherein the threshold temperature is higher than 60° C.

20. The device according to claim 16, wherein the threshold temperature is higher than 80° C.

21. The device as claimed in claim 16 wherein the insert material is a resin or wax material.

22. The device as claimed in claim 16 wherein the insert material has a melting point less than 120° C.

* * * * *